(12) United States Patent
Sietsma et al.

(10) Patent No.: US 8,263,522 B2
(45) Date of Patent: *Sep. 11, 2012

(54) METAL NITRATE CONVERSION METHOD

(75) Inventors: Jelle Rudolf Anne Sietsma, Utrecht (NL); Adrianus Jacobus Van Dillen, Culemborg (NL); Petra Elisabeth De Jongh, Utrecht (NL); Krijn Pieter De Jong, Houten (NL)

(73) Assignee: Johnson Matthey PLC, London (GB)

( * ) Notice: Subject to any disclaimer, the term of this patent is extended or adjusted under 35 U.S.C. 154(b) by 532 days.

This patent is subject to a terminal disclaimer.

(21) Appl. No.: 12/439,915

(22) PCT Filed: Aug. 14, 2007

(86) PCT No.: PCT/GB2007/050492
§ 371 (c)(1),
(2), (4) Date: Oct. 21, 2009

(87) PCT Pub. No.: WO2008/029177
PCT Pub. Date: Mar. 13, 2008

(65) Prior Publication Data
US 2010/0099553 A1 Apr. 22, 2010

(30) Foreign Application Priority Data
Sep. 7, 2006 (GB) .................. 0617529.3

(51) Int. Cl.
*B01J 23/74* (2006.01)
*B01J 21/08* (2006.01)
(52) U.S. Cl. ........ 502/259; 502/258; 502/260; 502/325; 502/337; 502/338
(58) Field of Classification Search .................. 502/258, 502/259, 260, 325, 337, 338
See application file for complete search history.

(56) References Cited

U.S. PATENT DOCUMENTS

| | | | |
|---|---|---|---|
| 6,316,382 B1 | 11/2001 | Kasztelan | |
| 2003/0064885 A1* | 4/2003 | Krylova et al. | ........... 502/325 |

FOREIGN PATENT DOCUMENTS

| | | |
|---|---|---|
| EP | 0 421 502 A2 | 4/1991 |
| WO | WO-2007/071899 A1 | 6/2007 |

OTHER PUBLICATIONS

R. W. Lines; J. G. Harfield; W. D. Griffiths; A. P. Rood; and M. Alderliesten, "Standardisation in Particle Sizing," *Anal. Proc.*, May 1984, vol. 21, pp. 159-172.

*Kirk-Othmer Encyclopedia of Chemical Technology*, Second Completely Revised Edition, vol. 2: Aluminum Compounds to Azo Dyes (New York: The Interscience Encyclopedia, Inc., 1963), pp. 40-57.

P. Scherrer, "Bestimmung der Grösse und der inneren Struktur von Kolloidteilchen mittels Röntgenstrahlen," Nachrichten von der Königl. Gesellschaft der Wissenschaften zu Göttingen, Mathematisch-physikalische Klasse, 1918, pp. 98-100. With English translation: "Analysis of the size and the internal structure of colloid particles by means of x-rays."

S. Brunauer, P. H. Emmett, and E. Teller, "Adsorption of Gases in Multimolecular Layers," *J. Am. Chem. Soc.*, 1938, vol. 60, No. 2, pp. 309-319.

E. P. Barrett, L. G. Joyner, and P. P. Halenda, "The Determination of Pore Volume and Area Distributions in Porous Substances. I. Computations from Nitrogen Isotherms," *J. Am. Chem. Soc.*, 1951, vol. 73, No. 1, pp. 373-380.

S. G. Marchetti, M. V. Cagnoli; A M. Alvarez; J. F. Bengoa; N. G. Gallegos, A. A. Yeramián; and R. C. Mercader, "Iron Uniform-Size Nanoparticles Dispersed on MCM-41 Used as Hydrocarbon Synthesis Catalyst," *Hyperfine Interactions*, 2002, 139/140, pp. 33-40.

J. F. Bengoa et al., "Iron oxide nanoparticles inside the MCM-41 channels: Study of the structural stability of the support," *Microporous and Mesoporous Materials*, 2005, vol. 84, pp. 153-160.

R. Köhn et al., "Studies on the state of iron oxide nanoparticles in MCM-41 and MCM-48 silica materials," *Microporous and Mesoporous Materials*, 2003, vol. 63, pp. 125-137.

D. L. Huber, "Synthesis, Properties, and Applications of iron Nanoparticles," *Small*, 2005, vol. 1, No. 5, pp. 482-501.

Hongfang Li et al., "Nickel oxide nanocrystallites within the wall of ordered mesoporous carbon CMK-3: Synthesis and characterization," *Microporous and Mesoporous Materials* 89 (2006), pp. 196-203.

Choi, "Reduction of supported cobalt catalysts by hydrogen," *Catalysis Letters*, 35 (1995), pp. 291-296.

Final Office Action dated May 5, 2010, from U.S. Appl. No. 12/158,854.

* cited by examiner

*Primary Examiner* — Elizabeth Wood
(74) *Attorney, Agent, or Firm* — RatnerPrestia

(57) ABSTRACT

A method for converting a supported metal nitrate into the corresponding supported metal oxide comprises heating the metal nitrate to effect its decomposition under a gas mixture that contains nitrous oxide and has an oxygen content of <5% by volume. The method provides very highly dispersed metal oxide on the support material. The metal oxide is useful as a catalyst or as a catalyst precursor.

11 Claims, 3 Drawing Sheets

METAL NITRATE CONVERSION METHOD

CROSS-REFERENCE TO RELATED APPLICATIONS

This application is the U.S. National Phase application of PCT International Application No. PCT/GB2007/050492, filed Aug. 14, 2007, and claims priority of British Patent Application No. 0617529.3, filed Sep. 7, 2006, both of which are incorporated herein by reference.

FIELD OF THE INVENTION

This invention relates to methods for conversion of metal nitrates into the corresponding metal oxides.

BACKGROUND OF THE INVENTION

Metal nitrates are useful metal oxide precursors due to their relatively low cost and ease of manufacture. They are often converted into the corresponding metal oxides in catalyst or sorbent manufacture. In catalyst or sorbent manufacture typically one or more soluble metal nitrates is impregnated onto a suitable support material, and dried to remove the solvent. The impregnated support is then usually heated under air, in a step often called calcination, to an elevated temperature at or above the decomposition temperature of the metal nitrate to form the metal oxide. However, such a method does not always lead to satisfactory oxidic materials. In particular, where the metal oxide is a reducible metal oxide, the dispersion and distribution of crystallites of the metal oxide and hence reduced metal obtained by these processes is often poor.

Variations on this preparative method have been attempted. EPO421502 describes a process for the preparation of a catalyst or catalyst precursor wherein cobalt nitrate supported on a porous inert carrier is calcined in an atmosphere containing at least 20% by volume nitrogen oxide (not taking the water content of the atmosphere into consideration). The nitrogen oxides preferably originated from the decomposition of cobalt nitrate under conditions where the calcination oven was not purged or purged at low velocity. Such calcination was stated to produce agglomerates of cobalt oxide crystallites with dimensions in the range 1 to 10 micrometres.

In the aforesaid EPO421502 calcination of the cobalt nitrate was performed in air, with the nitrogen oxide being provided by the metal nitrate itself. Whereas the specific nitrogen oxide was not stated, the nitrogen oxide predominant during such calcination will be nitrogen dioxide ($NO_2$).

Supported metal oxides find use as catalysts, catalyst precursors and sorbents whose effectiveness is related to the dispersion of the metal oxide on the support. Therefore there is a desire to improve the dispersion of metal oxides derived from metal nitrates.

SUMMARY OF THE INVENTION

We have found that heat treatment under a gas mixture that specifically contains nitrous oxide ($N_2O$), and that contains no or low amounts of oxygen leads to very highly dispersed and uniformly distributed supported metal oxides. In contrast to the method of EPO421502, high concentrations of nitrogen oxide are not required in the method of the present invention and the method provide extremely small metal oxide agglomerates having a crystallite size <10 nanometres.

Accordingly the invention provides a method for converting a supported metal nitrate into the corresponding supported metal oxide comprising heating the metal nitrate to effect its decomposition under a gas mixture containing nitrous oxide and having an oxygen content of <5% by volume.

The invention further provides a supported metal oxide obtainable by the above method.

BRIEF DESCRIPTION OF THE DRAWINGS

The invention is further illustrated by reference to FIGS. 1-3, in which.

DETAILED DESCRIPTION OF THE INVENTION

Figure 1:
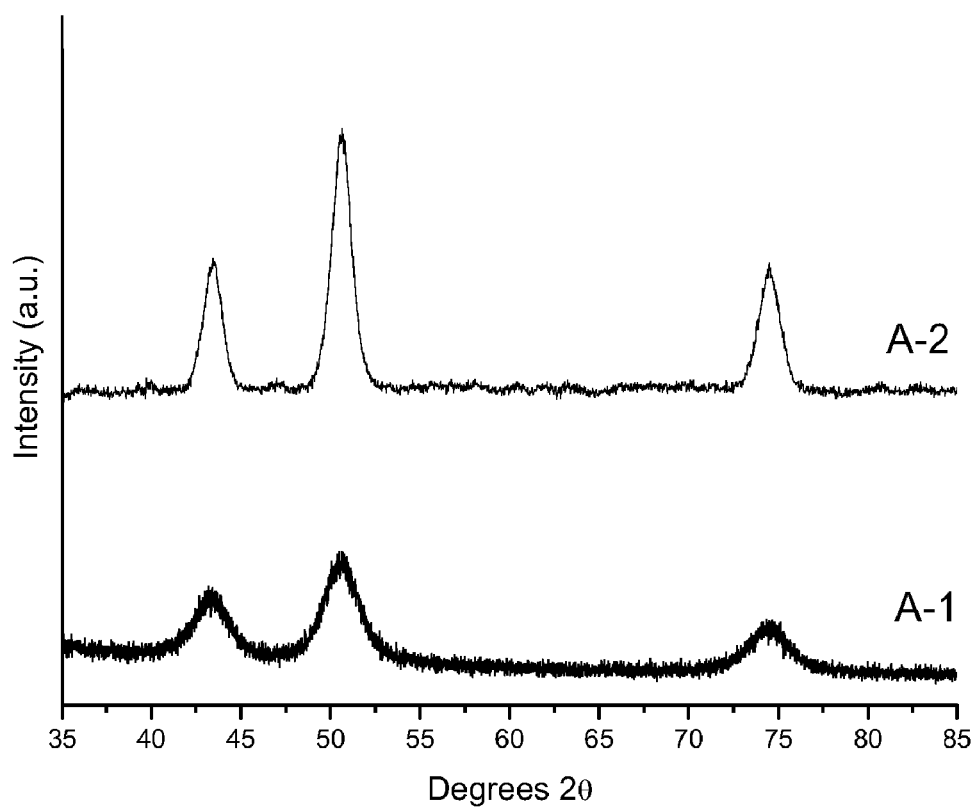
FIG. 1 depicts XRD patterns of a silica supported nickel oxide prepared according to the invention (A-1) and not according to the invention (A-2)

Thus method of the present invention comprises exposing the supported metal nitrate to a gas mixture that contains nitrous oxide and has an oxygen content of <5% by volume, and heating the metal nitrate exposed to this gas mixture to at least its decomposition temperature. Hence, in the present invention the nitrous oxide is not generated by decomposition of the metal nitrate but should be present in the gas mixture to which the metal nitrate is exposed during decomposition.

The metal nitrate may be supported in a number of ways including dry mixing, molten nitrate mixing, precipitation and impregnation. Impregnation is preferred. For example the metal nitrate may be impregnated onto a support material from an aqueous or non-aqueous solution, e.g. ethanol, which may include other materials, and then dried to remove the solvent or solvents. One or more metal nitrates may be present in the solution. One or more impregnation steps may be performed to increase metal loading or provide sequential layers of different metal nitrates prior to drying. Impregnation may be performed using any of the methods known to those skilled in the art of catalyst or sorbent manufacture, but preferably is by way of a so-called 'dry' or 'incipient-wetness' impregnation as this minimises the quantity of solvent used and to be removed in drying. Incipient wetness impregnation is particularly suitable for porous support materials and comprises mixing the support material with only sufficient solution to fill the pores of the support.

Drying may be performed using known methods at reduced pressure, atmospheric pressure or elevated pressure, including spray drying and freeze drying. The temperature of the drying step is preferably ≦200° C., more preferably ≦160° C. to minimise premature degradation of the metal nitrate. The drying step may be performed under air or another oxygen containing gas, or an inert gas such as nitrogen, helium or argon.

The supported metal nitrate will therefore comprise one or more metal nitrates on the surface and/or in the pores of the support.

The metal nitrate is heated to bring about its decomposition by heating it to, or if desired above, its decomposition temperature at which it forms the metal oxide. This heating step is different from drying (which principally acts to remove solvent) by causing a physio-chemical conversion of the metal nitrate to the corresponding metal oxide. It will be understood that in the method of the present invention a supported metal nitrate may, if desired, be dried and heated to decomposition in a single operation. The temperature to which the metal nitrate is raised to bring about its decomposition may be in the range 100-1200° C., but preferably the temperature is in the range 200-600° C. to ensure conversion of the nitrate to the oxide while at the same time minimising sintering of the oxide. However, where it is desired to form spinel or perovskite oxide phases on or with the support, it may be desirable to use temperatures in the range 500-1200° C. The time at which the supported metal nitrate is at a temperature within these ranges range is preferably <16 hours, more preferably <8 hours.

Preferably at least 90% wt, more preferably at least 95%, most preferably at least 99% of the metal nitrate is converted into the corresponding metal oxide.

It is a feature of the present invention that the atmosphere to which the supported metal nitrate is exposed during heating contains very little or no free oxygen as this has been found to be a source of poor metal oxide dispersion in nitrate-derived materials. Hence the oxygen ($O_2$) content of the gas stream is <5%, preferably <1%, most preferably <0.1% by volume.

The gas stream to which the metal nitrate is exposed may be any gas stream that contains nitrous oxide and has <5% oxygen by volume. Preferably the gas stream comprises one or more gases selected from carbon monoxide, carbon dioxide or an inert gas. Preferably the inert gas is one or more selected from nitrogen, helium or argon. Preferably the gas stream to which the supported metal oxide is exposed consists of one or more inert gases and nitrous oxide.

The gas mixture may be at or above atmospheric pressure, typically up to about 10 bar abs. Various methods, known in the art for performing the heating step may be used. For example a reducing gas stream may be passed through a bed of particulate supported metal nitrate. Where the heating step is performed by passing the gas mixture through a bed of the supported metal oxide, the gas-hourly-space-velocity (GHSV) of the gas mixture is preferably in the range of 100-600000 $h^{-1}$, more preferably 600-100000 $h^{-1}$, most preferably 1000-60000 $h^{-1}$.

The nitrous oxide concentration in the gas stream is preferably in the range 0.001 to 15% by volume, more preferably 0.01 to 10% vol, most preferably 0.1 to 5% vol to minimise scrubbing requirements.

The metal nitrate may be any metal nitrate but is preferably a nitrate of a metal used in the manufacture of catalysts, catalyst precursors or sorbents. The metal nitrate may be an alkali-, alkali metal- or transition metal-nitrate. Preferably the metal nitrate is a transition metal nitrate, i.e. a nitrate of metals selected from Groups 3-12 inclusive of the Periodic Table of the Elements. Suitable metal readily available nitrates for catalyst, catalyst precursor or sorbent manufacture include nitrates of La, Zr, Cr, Mn, Fe, Ru, Co, Rh, Ir, Ni, Pd, Pt, Cu and Zn, more preferably nitrates of Cr, Mn, Fe, Ru, Co, Rh, Ir, Ni, Pd, Pt, Cu and Zn.

By the term "metal nitrate" we include metal nitrate compounds of formula $M(NO_3)_x.(H_2O)_a$ where x is the valency of the metal M, and 'a' may be $\geq 0$ or an integer and also partial decomposition products of such compounds formed for example during a previous drying step, such as metal hydroxy nitrates.

We have found the present process particularly useful for producing highly dispersed reducible metal oxides, i.e. a metal oxide in which at least part of the metal may be reduced using a reducing gas stream, such as carbon monoxide and/or hydrogen, to its elemental form. Such reducible metal oxides include those of Ni, Co, Cu and Fe and therefore in a preferred embodiment, the metal nitrate is a nitrate of nickel, cobalt, copper, or iron, more preferably nickel or cobalt, especially nickel.

The support onto which the metal nitrate may be supported may be a metal, carbon, metal oxide, mixed metal oxide or solid polymer support. For example, the support may be a single or mixed metal oxide including silica or silicates, or another type of support useful in catalyst or sorbent manufacture, for example, metals, metal alloys or carbons. One or more supports may be used in the present invention.

Carbon supports, such as activated carbons, high surface area graphites, carbon nanofibres, and fullerenes in powder, pellet or granular form and having suitable porosities, e.g. above 0.1 ml/g may be used as supports for the present invention, preferably where the gas stream contains <0.1% oxygen by volume. Such supports cannot be used in prior art methods where air calcination is used.

Preferably the support is an oxidic support, which may be a single- or mixed metal oxide material, including ceramics, zeolites, perovskites, spinels and the like. The oxidic support may also be in the form of a wash-coat on a ceramic, metal, carbon or polymer substrate.

The support may be in the form of a powder having a surface-weighted mean diameter D[3,2] in the range 1 to 200 microns. The term surface-weighted mean diameter D[3,2], otherwise termed the Sauter mean diameter, is defined by M. Alderliesten in the paper "A Nomenclature for Mean Particle Diameters"; Anal. Proc., vol 21, May 1984, pages 167-172, and is calculated from the particle size analysis, which may conveniently be effected by laser diffraction for example using a Malvern Mastersizer. Agglomerates of such powders having particle sizes in the range 200 microns to 1 mm may also be used as the support. Alternatively the support may be in the form of shaped units such as pellets, extrudates or granules typically having particle sizes in the range 1-25 mm and an aspect ratio of less than 2. (By particle size we mean the smallest particle dimension such as width, length or diameter). Alternatively the support may be in the form of a monolith, e.g. a honeycomb, or a cellular material such as an open foam structure.

The support is preferably selected from alumina, metal-aluminate, silica, aluminosilicate, titania, zirconia or mixtures of these, including co-gels, either in powder, shaped unit, monolithic or cellular form.

The support may be a silica support. Silica supports may be formed from natural sources, e.g. as kieselguhr, may be a pyrogenic or fumed silica or may be a synthetic, e.g. precipitated silica or silica gel. Ordered mesoporous silicas, such as SBA-15 may be used as a support. Precipitated silicas are preferred. The silica may be in the form of a powder or a shaped material, e.g. as extruded, pelleted or granulated silica pieces. Suitable powdered silicas typically have particles of surface weighted mean diameter D[3,2] in the range 3 to 100 μm. Shaped silicas may have a variety of shapes and particle sizes, depending upon the mould or die used in their manufacture. For example the particles may have a cross-sectional shape which is circular, lobed or other shape and a length from about 1 to greater than 10 mm. The BET surface area of suitable powdered or granular silicas is generally in the range 10-500 $m^2/g$, preferably 100-400 $m^2 \cdot g^{-1}$. The pore volume is generally between about 0.1 and 4 $ml \cdot g^{-1}$, preferably 0.2-2 $ml \cdot g^{-1}$ and the mean pore diameter is preferably in the range from 0.4 to about 30 nm. If desired, the silica may be mixed with another metal oxide, such as titania or zirconia. The silica may alternatively be present as a coating on a shaped unit, which is preferably of alumina typically as a coating of 0.5 to 5 monolayers of silica upon the underlying support.

The support may be a titania support. Titania supports are preferably synthetic, e.g. precipitated titanias. The titania may optionally comprise e.g. up to 20% by weight of another refractory oxide material, typically silica, alumina or zirconia. The titania may alternatively be present as a coating on a support which is preferably of silica or alumina, for example as a coating of 0.5 to 5 monolayers of titania upon the underlying alumina or silica support. The BET surface area of suitable titania is generally in the range 10-500 $m^2 \cdot g^{-1}$, preferably 100 to 400 $m^2 \cdot g^{-1}$. The pore volume of the titania is preferably between about 0.1 and 4 $ml \cdot g^{-1}$, more preferably 0.2 to 2 $ml \cdot g^{-1}$ and the mean pore diameter is preferably in the range from 2 to about 30 nm.

Similarly zirconia supports may be synthetic, e.g. precipitated zirconias. The zirconia may again optionally comprise e.g. up to 20% by weight of another refractory oxide material, typically silica, alumina or titania. Alternatively the zirconia may be stabilised e.g. an yttria- or ceria-stabilised zirconia. The zirconia may alternatively be present as a coating on a support, which is preferably of silica or alumina, for example as a coating of 0.5 to 5 monolayers of zirconia upon the underlying alumina or silica support.

The support may be a metal aluminate, for example a calcium aluminate.

The support material may be a transition alumina. Transition aluminas are defined in "Ullmans Encyklopaedie der technischen Chemie", 4, neubearbeitete und erweiterte Auflage, Band 7 (1974), pp. 298-299. Suitable transition alumina may be of the gamma-alumina group, for example eta-alumina or chi-alumina. These materials may be formed by calcination of aluminium hydroxides at 400 to 750° C. and generally have a BET surface area in the range 150 to 400 $m^2 \cdot g^{-1}$. Alternatively, the transition alumina may be of the delta-alumina group which includes the high temperature forms such as delta- and theta-aluminas which may be formed by heating a gamma group alumina to a temperature above about 800° C. The delta-group aluminas generally have a BET surface area in the range 50 to 150 $m^2 \cdot g^{-1}$. Alternatively, the transition alumina may be alpha-alumina. The transition aluminas contain less than 0.5 mole of water per mole of $Al_2O_3$, the actual amount of water depending on the temperature to which they have been heated. A suitable transition alumina powder generally has a surface-weighted mean diameter D[3,2] in the range 1 to 200 μm. In certain applications such as for catalysts intended for use in slurry reactions, it is advantageous to use very fine particles which are, on average, preferably less than 20 μm, e.g. 10 μm or less. For other applications e.g. as a catalyst for reactions carried out in a fluidised bed, it may be desirable to use larger particle sizes, preferably in the range 50 to 150 μm. It is preferred that the alumina powder has a relatively large average pore diameter as the use of such aluminas appears to give catalysts of particularly good selectivity. Preferred aluminas have an average pore diameter of at least 10 nm, particularly in the range 15 to 30 nm. [By the term average pore diameter we mean 4 times the pore volume as measured from the desorption branch of the nitrogen physisorption isotherm at 0.98 relative pressure divided by the BET surface area]. Preferably, the alumina material is a gamma alumina or a theta alumina, more preferably a theta alumina, having a BET surface area of 90-120 $m^2 \cdot g^{-1}$ and a pore volume of 0.4-0.8 $cm^3 \cdot g^{-1}$. The alumina support material may be in the form of a spray dried powder or formed into shaped units such as spheres, pellets, cylinders, rings, or multi-holed pellets, which may be multi-lobed or fluted, e.g. of cloverleaf cross-section, or in the form of extrudates known to those skilled in the art. The alumina support may be advantageously chosen for high filterability and attrition resistance.

The present invention may be used to convert metal nitrates on any support material, however, certain metal nitrate/support combinations are more preferred. For example, depending upon the metal it may be, or may not be, desirable to combine the metal nitrate with a support that is able, under the heating conditions used to decompose the metal nitrate, form mixed metal oxide compounds with the resulting supported metal oxide. Low-activity supports such as carbon or alpha-alumina may be used to reduce or prevent mixed-metal oxide formation with the support where this is undesired.

As stated above, we have found the process of the present invention to be particularly useful for preparing highly dispersed reducible metal oxides on supports. Therefore in one embodiment, the process further comprises heating the supported reducible metal oxide under a reducing gas stream to effect reduction of at least a part of the metal oxide. Any reducing gas stream may be used however preferably the reducing gas stream comprises carbon monoxide and/or hydrogen.

Accordingly the invention further provides a supported reduced metal oxide obtainable by the above method. A supported reduced metal oxide will comprise a metal in the elemental form, and possibly unreduced metal oxide, on the support material. In addition, other, reducible or non-reducible metal oxides may be present on the support.

In this embodiment, the supported metal oxide comprises at least one reducible metal oxide; preferably one or more selected from nickel oxide, cobalt oxide, copper oxide or iron oxide and the reduction is preferably performed with a hydrogen-containing gas.

Thus a reduction step may be performed by passing a hydrogen-containing gas such as hydrogen, synthesis gas or a mixture of hydrogen with nitrogen, methane or other inert gas over the supported reducible metal oxide at elevated temperature, for example by passing the hydrogen-containing gas over the composition at temperatures in the range 150-600° C., preferably 300-500° C. for between 0.1 and 24 hours, at atmospheric or higher pressures up to about 25 bar. The optimum reducing conditions for nickel oxide, cobalt oxide, copper oxide or iron oxides are known to those skilled in the art.

In the supported reduced metal oxides prepared by the method of the present invention preferably at least 50%, more preferably >80% and most preferably >90% of the reducible metal oxide is reducible to the elemental active form. Reduced metal oxides with very high metal dispersions, expressed as metal surface area per gram catalyst or gram metal in the reduced material may be obtained by the method of the present invention. Metal surface areas may conveniently be determined by chemisorption (e.g. hydrogen chemisorption) using methods known to those skilled in the art.

The supported metal oxides and reduced metal oxides have considerably higher metal oxide and metal dispersions than the metal oxide and reduced metal oxides obtainable using prior art methods. This is because the decomposition of the metal nitrate in the presence of the nitrous oxide in a gas stream having <5% by volume oxygen prevents the sintering that would otherwise occur.

The supported metal oxides of the present invention have been found by Scanning Transmission Electron Microscopy (STEM) and X-Ray ° Diffraction (XRD) to have metal oxide crystallite sizes of less than 10 nanometres, preferably less than 7 nanometres at resulting metal oxide loadings on the supports of up to 30% by weight. The crystallite sizes of the supported reduced metal oxides are also <10 nm, preferably <7 nm.

The supported metal oxides and supported reduced metal oxides may be used in many fields of technology. Such areas include catalyst, catalyst precursors, sorbents, semi-conductors, superconductors, magnetic storage media, solid-state storage media, pigments and UV-absorbents. Preferably, the supported metal oxides and supported reduced metal oxides are used as catalysts, catalyst precursors or sorbents. By the term "sorbents" we include adsorbents and absorbents.

For example reduced supported Cu oxides such as $Cu/ZnO/Al_2O_3$ are used as methanol synthesis catalysts and water-gas shift catalysts. Reduced supported Ni, Cu and Co oxides may be used alone or in combination with other metal oxides, e.g. Zn oxide, as catalysts for hydrogenation reactions and the reduced Fe or Co oxides may be used as catalysts for the Fischer-Tropsch synthesis of hydrocarbons. Reduced Fe catalysts may also be used in high-temperature shift reactions and in ammonia synthesis.

In preferred embodiments, the supported metal oxides and supported reduced metal oxides are used a catalysts in hydrogenation reactions and the Fischer-Tropsch synthesis of hydrocarbons. These catalysts may in addition to the Ni, Cu, Co or Fe, further comprise one or more suitable additives and/or promoters useful in hydrogenation reactions and/or Fischer-Tropsch catalysis. For example, the Fischer-Tropsch catalysts may comprise one or more additives that alter the physical properties and/or promoters that effect the reducibility or activity or selectivity of the catalysts. Suitable additives are selected from compounds of potassium (K), molybdenum (Mo), nickel (Ni), copper (Cu), iron (Fe), manganese (Mn), titanium (Ti), zirconium (Zr), lanthanum (La), cerium (Ce), chromium (Cr), magnesium (Mg) or zinc (Zn). Suitable promoters include rhodium (Rh), iridium (Ir), ruthenium (Ru), rhenium (Re), platinum (Pt) and palladium (Pd). Preferably one or more promoters selected from Ru, Re, Pt or Pd is included in the catalyst precursor. Additives and/or promoters may be incorporated into the catalysts by use of suitable compounds such as acids, e.g. perrhenic acid, metal salts, e.g. metal nitrates or metal acetates, or suitable metal-organic compounds, such as metal alkoxides or metal acetylacetonates. The amount of promoter metal may be varied between 3 and 50%, preferably between 5 and 20% by weight on reducible metal.

As stated above, supported reduced metal oxide catalysts may be used for example for hydrogenation reactions and for the Fischer-Tropsch synthesis of hydrocarbons.

Typical hydrogenation reactions include the hydrogenation of aldehydes and nitriles to alcohols and amines respectively, and the hydrogenation of cyclic aromatic compounds or unsaturated hydrocarbons. The catalysts of the present invention are particularly suitable for the hydrogenation of unsaturated organic compounds particularly oils, fats, fatty acids and fatty acid derivatives like nitriles. Such hydrogenation reactions are typically performed in a continuous or batch-wise manner by treating the compound to be hydrogenated with a hydrogen-containing gas under pressure in an autoclave at ambient or elevated temperature in the presence of the catalyst, for example the hydrogenation may be carried out with hydrogen at 80-250° C. and a pressure in the range $0.1$-$5.0 \times 10^6$ Pa.

The Fischer-Tropsch synthesis of hydrocarbons is well established. The Fischer-Tropsch synthesis converts a mixture of carbon monoxide and hydrogen to hydrocarbons. The mixture of carbon monoxide and hydrogen is typically a synthesis gas having a hydrogen:carbon monoxide ratio in the range 1.7-2.5:1. The reaction may be performed in a continuous or batch process using one or more stirred slurry-phase reactors, bubble-column reactors, loop reactors or fluidised bed reactors. The process may be operated at pressures in the range 0.1-10 Mpa and temperatures in the range 150-350° C. The gas-hourly-space-velocity (GHSV) for continuous operation is in the range 100-25000 $h^{-1}$. The catalysts of the present invention are of particular utility because of their high metal surface areas/g catalyst.

EXAMPLE 1

SBA-15 Supported Nickel Oxide

SBA-15 powder (BET surface area=637 $m^2 \cdot g^{-1}$, total pore volume=0.80 $cm^3 \cdot g^{-1}$) was impregnated to incipient wetness with an aqueous nickel (II) nitrate solution to provide 20 wt % $Ni/SiO_2$. After impregnation an equilibration time of 15 minutes was applied. Subsequently the impregnated solid was dried by heating the product from 25° C. to a final temperature of 120° C. and applying a heating rate of 1° C. $min^{-1}$. The sample was kept at the final temperature for 720 minutes. This dried sample was denoted sample A. From this sample a small amount (40 mg) was given a second heat treatment using a plug flow reactor with a diameter of 1 cm and length of 17 cm. The sample was heated from 25° C. to 450° C. using a heating rate of 1° C.$\cdot min^{-1}$ and held for 240 minutes at 450° C. in a flow of helium containing 1% by volume nitrous oxide ($N_2O$) or in air (viz. calcination). The sample thermally treated according to the present invention in a gas stream of helium containing 1% by volume nitrous oxide ($N_2O$) was designated A-1 while the air-calcined sample, not according to the present invention, was denoted as A-2. The preparative conditions are summarised in Tables 1-3.

TABLE 1

| Impregnation conditions | |
|---|---|
| Support | SBA-15 powder |
| Support quantity (g) | 0.25 |
| Solvent | Demineralized water |
| Precursor salt | $Ni(NO_3)_2 \cdot 6H_2O$ |
| Concentration precursor solution (M) | 4.23 |
| Impregnation | 60 mbar |
| | incipient wetness |
| | no rotation |
| Equilibration time (min) | 15 |

TABLE 2

| Drying conditions | |
|---|---|
| Starting temperature (° C.) | 25 |
| Final temperature (° C.) | 120 |
| Heating rate (° C. $min^{-1}$) | 1 |
| Time at final temperature (min) | 720 |
| Atmosphere | air |

TABLE 3

Temperature and gas flow profile second thermal treatment

| Step N° | Duration (min) | $T_{start}$ (° C.) | $T_{final}$ (° C.) | Heating Rate (° C. $\cdot min^{-1}$) | He (ml $\cdot min^{-1}$) | $N_2O/He^*$ or air (ml $\cdot min^{-1}$) |
|---|---|---|---|---|---|---|
| 1 | 10 | 25 | 25 | 0 | 90 | 0 |
| 2 | 425 | 25 | 450 | 1 | 0 | 90 |
| 3 | 240 | 450 | 450 | 0 | 0 | 90 |
| 4 | 45 | 450 | 25 | −10 | 90 | 0 |

*concentration premixed gas bottle is 1 v/v % $N_2O/He$

Characterisation was carried out using X-ray powder diffraction (XRD), scanning transmission electron microscopy (STEM) and nitrogen physisorption.

XRD patterns were recorded at room temperature from 35 to 85° 2θ with a Bruker-Nonius D8 Advance X-ray Diffractometer setup using Co—K$_{\alpha 12}$ (λ=1.79026 Å) radiation. The average nickel oxide crystal size was calculated according to the Scherrer equation [see Scherrer, P. Göttinger Nachrichten 2 (1938) 98] and using the most intense reflection at 2θ=50.8°. STEM images were obtained using a Tecnai 20 FEG microscope that operates at 200 kV. The average nickel oxide particle size was determined by the diameter of typically 50 particles. Nitrogen physisorption isotherms were obtained at 77 K using a Micromeritics Tristar 3000 apparatus. Prior to analysis the samples were dried for 14 hours at 120° C. under a stream of helium.

The XRD pattern of sample A-2 (FIG. 1) shows that large nickel oxide (NiO) crystallites are present after the thermal treatment in air (i.e. calcination) of dried sample A. However, very small NiO crystallites are found when the dried sample is treated according to the process of the present invention, namely a diluted stream of nitrous oxide (A-1). The observed average crystallite sizes for the samples A-1 and A-2 are given in Table 4.

TABLE 4

Observed of average nickel oxide crystallite sizes

| Sample | Gas composition thermal treatment | $d_{XRD}$ (nm) | $d_{TEM}$ (nm) |
|---|---|---|---|
| A-1 | N$_2$O/He | 5 | 4-6 |
| A-2 | Air | 10 | 10-100* |

*crystallites present inside the pores of SBA-15 are mostly anisotropic

Figure 2:
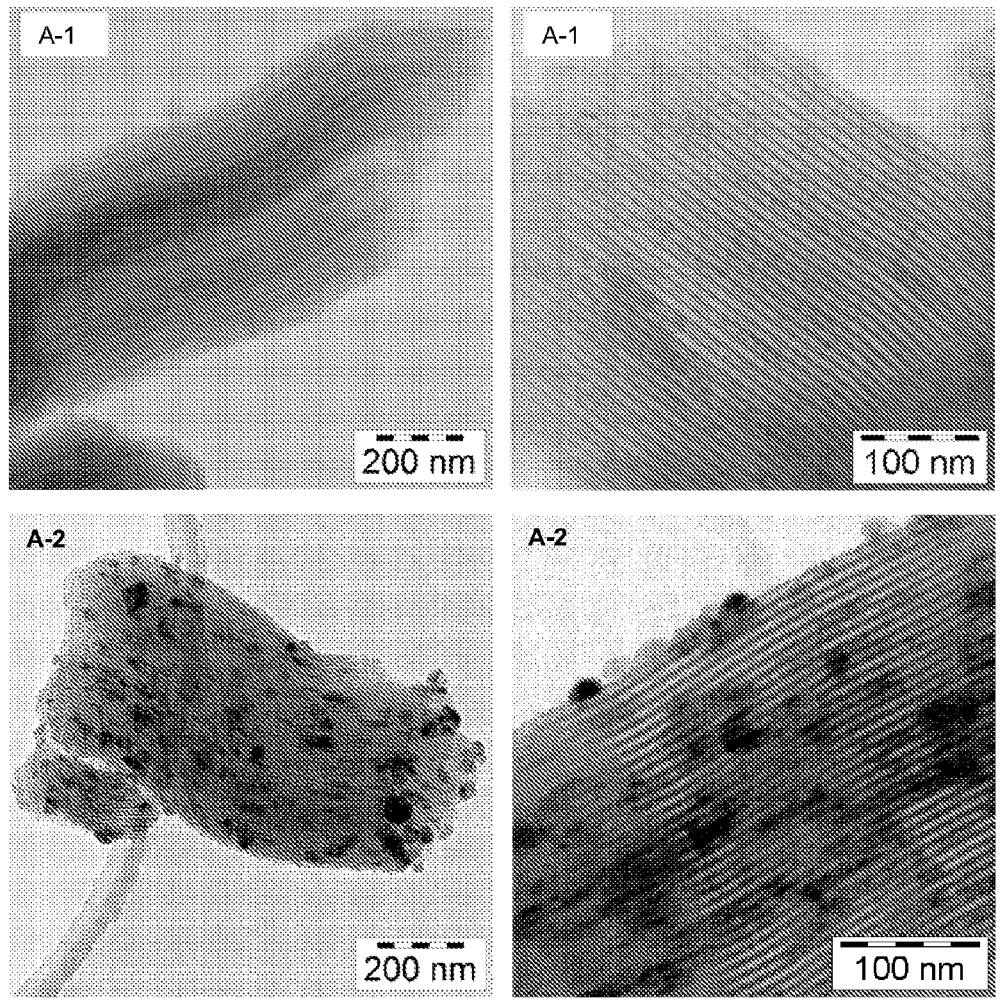
FIG. 2 depicts bright-field STEM micrographs of the silica-supported nickel oxides (A-1, A-2)

Two typical bright-field STEM images of both the samples A-1 and A-2 are depicted in FIG. 2. The images demonstrate that the ordered pore structure of SBA-15 formed by cylindrically shaped open mesopores was retained in both samples. In more detail, the images of sample A-2 prepared by air calcination show that the nickel oxide particles are deposited inhomogenously over the support and have a broad particle size distribution. Moreover, the nickel oxide particles inside the mesoporous channels appear to have been restricted in growth in one dimension by the pore wall of the mesopores yielding anisotropic particles that plug the pores of SBA-15. Furthermore, nickel oxide particles are present that are larger than the pore diameter. These particles appear to be located at the exterior surface area of the support. The STEM image recorded at higher magnification clearly demonstrates that nickel oxide is present at the exterior surface of the SBA-15 particles.

The STEM images of the sample A-1 prepared according to the present invention clearly show that highly dispersed and homogeneously distributed nickel oxide is present throughout the pores of SBA-15. No nickel oxide particles are found at the exterior surface area of the support. A comparison between the NiO particle size distributions found in both the samples A-1 and A-2 can be found in Table 4.

Figure 3:
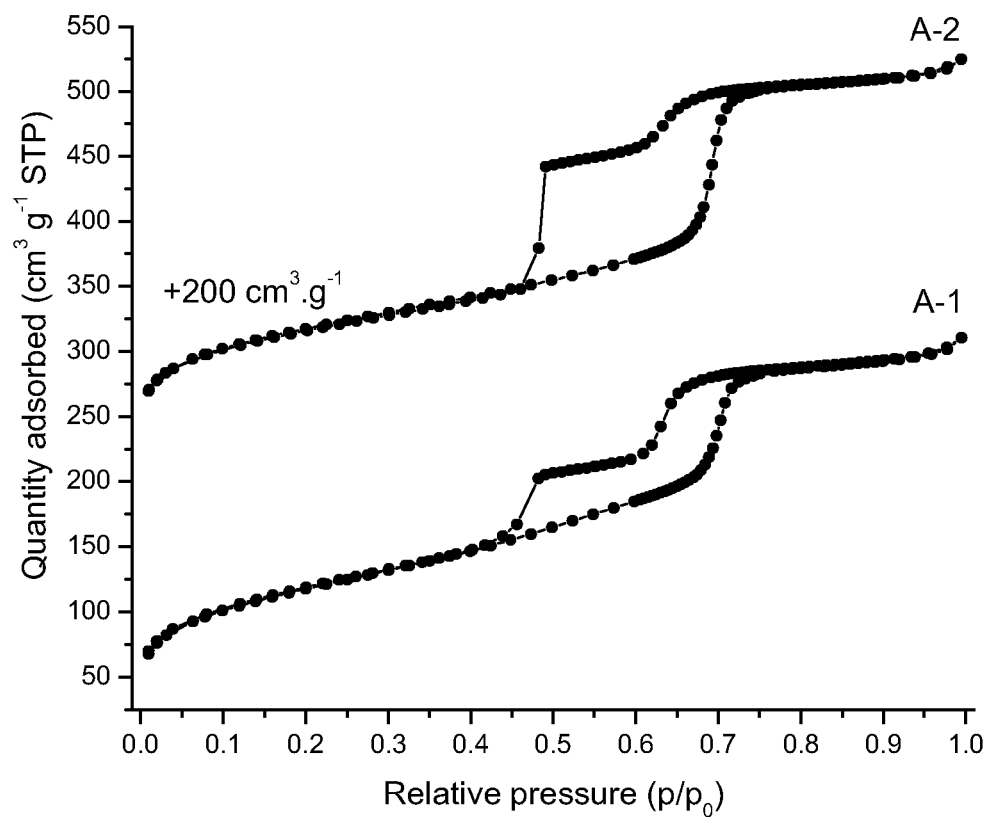
FIG. 3 depicts nitrogen physisorption isotherms of the silica-supported nickel oxides (A-1, A-2).

The nitrogen physisorption adsorption isotherm of samples A-2 (FIG. 3) contains all typical features reported for SBA-15. This indicates that the air calcination had not induced major damage to the support structure. However, the recorded desorption branch of this sample contains a forced closure of the desorption branch located at a relative pressure of approximately 0.48. This forced closure can be attributed to blocking of the mesoporous channels of SBA-15 by nickel oxide crystallites. These nickel oxide plugs create ink-bottle type pores that result in the observed forced closure of the isotherm during desorption. Comparison of this isotherm with that of sample A-1 prepared according to the present invention clearly shows that the degree of pore blocking had significantly decreased because of the formation of small nickel oxide particles.

The invention claimed is:

1. A method for converting a supported metal nitrate into the corresponding supported metal oxide comprising heating the metal nitrate to effect its decomposition under a gas mixture containing nitrous oxide and having an oxygen content of <5% by volume, wherein the nitrous oxide concentration in the gas mixture is in the range 0.001 to 15% by volume, wherein the metal nitrate is impregnated onto a support material from a solution and dried to remove the solvent before heating the metal nitrate to convert it to the corresponding metal oxide.

2. A method according to claim 1 wherein the gas mixture consists of one or more inert gases and nitrous oxide.

3. A method according to claim 2 wherein the one or more inert gas is selected from the group consisting of nitrogen, helium and argon.

4. A method according to claim 1 wherein the supported metal nitrate is heated to a temperature in the range 100-1200° C.

5. A method according to claim 1 wherein the metal nitrate is a transition metal nitrate.

6. A method according to claim 1 wherein the metal nitrate is a nitrate of nickel, cobalt, copper, or iron.

7. A method according to claim 1 wherein the support is a metal, carbon, metal oxide, mixed metal oxide or solid polymer support.

8. A method according to claim 1 wherein the support is selected from the group consisting of alumina, metal-aluminate, silica, aluminosilicate, titania, zirconia or mixtures of these.

9. A method according to claim 1 wherein the supported metal oxide is a reducible metal oxide, further comprising heating the supported metal oxide under a reducing gas stream to effect reduction of at least a part of the metal oxide.

10. A method according to claim 9 wherein the reducing gas stream comprises at least one of carbon monoxide and hydrogen.

11. A method according to claim 9 wherein the supported metal oxide is nickel oxide, cobalt oxide, copper oxide or iron oxide and the reduction is performed with a hydrogen-containing gas.

* * * * *